(12) United States Patent
Boday et al.

(10) Patent No.: US 9,790,239 B1
(45) Date of Patent: Oct. 17, 2017

(54) POLYBOROAMINALS

(71) Applicant: International Business Machines Corporation, Armonk, NY (US)

(72) Inventors: Dylan J. Boday, Austin, TX (US); Jeannette M. Garcia, San Leandro, CA (US); James L. Hedrick, Pleasanton, CA (US); Rudy J. Wojtecki, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/166,105

(22) Filed: May 26, 2016

(51) Int. Cl.
  *C07F 9/46* (2006.01)
  *C07F 5/02* (2006.01)

(52) U.S. Cl.
  CPC .............. *C07F 5/027* (2013.01); *C07F 9/46* (2013.01)

(58) Field of Classification Search
  None
  See application file for complete search history.

(56) References Cited

U.S. PATENT DOCUMENTS

| | | |
|---|---|---|
| 4,734,472 A | 3/1988 | Chung |
| 4,751,276 A | 6/1988 | Chung |
| 5,286,800 A | 2/1994 | Chung et al. |
| 6,248,837 B1 | 6/2001 | Chung et al. |
| 7,179,940 B2 | 2/2007 | Vaultier et al. |

FOREIGN PATENT DOCUMENTS

| | | |
|---|---|---|
| CN | 104861297 A | 8/2015 |
| EP | 2684887 A1 | 1/2014 |
| JP | 2002317049 A | 10/2002 |

OTHER PUBLICATIONS

Matsumi et al, Macromolecules (2006), vol. 39, No. 20, pp. 6924-6927.*

* cited by examiner

*Primary Examiner* — Zinna Northington Davis
(74) *Attorney, Agent, or Firm* — Patterson + Sheridan, LLP

(57) ABSTRACT

Materials include compounds such as polyboroaminals of the formula, and salts or adducts thereof:

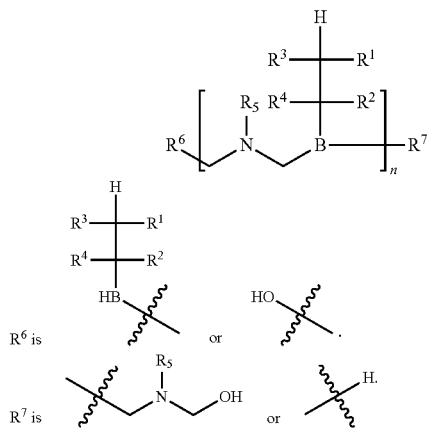

Each instance of $R^1$, $R^2$, $R^3$, and $R^4$ is independently —H or substituted or unsubstituted alkyl, cycloalkyl, alkenyl, alkoxyl, aryl, heterocyclyl or $R^3$ and $R^4$ combine to form a 5-membered cycloalkyl or heterocyclyl or 6-membered aryl, cycloalkyl or heterocyclyl. Each instance of $R^5$ is independently —H, halo, or alkyl. n is a positive integer and the number average molecular weight or weight average molecular weight of the compound of formula (I) is between about 2,000 to about 80,000.

24 Claims, No Drawings

POLYBOROAMINALS

FIELD

The present disclosure relates to polyboroaminals and synthesis of polyboroaminals.

BACKGROUND

Polythioaminals are a class of polymers with a variety of uses, including drug delivery. Some polythioaminals are polymers that have the general formula:

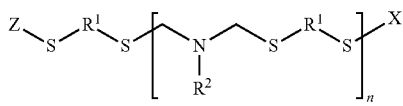

where $R^1$ and $R^2$ are organic or hetero-organic species. It has been shown that polythioaminals having the above structure may be synthesized by reacting an N-substituted hexahydrotriazine with a dithiol, as follows:

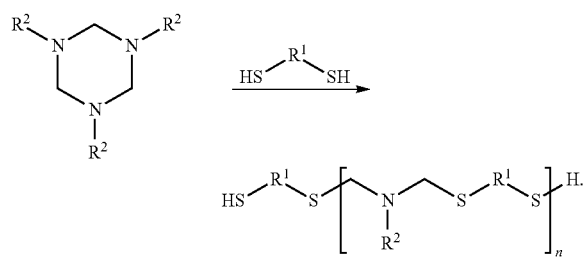

Subsequent reactions may replace the hydrogen atoms at the end of the thioaminal polymer with the X and Z groups above. These polymers feature dynamic covalent bonding, undergoing reversible bond breakage and reformation. The dynamic covalent character of these polymers is chemosensitive, and may be triggered by the presence of thiols.

However, polythioaminal formulas are limited in scope by monomer starting materials, one being the dithiol and the other being the hexahydrotriazine. Hexahydrotriazine may be formed in situ, but this synthesis is limited to thiol, aldehyde, and amine containing monomers. Furthermore, polythioaminals may be used for medical applications such as drug delivery. However, pharmacokinetic and pharmacodynamic limitations have been noted.

Therefore, there is a need in the art for new polythioaminal derivatives and methods for syntheses thereof.

SUMMARY

In some embodiments, a material includes compounds such as polyboroaminals of the formula, or a salt or an adduct thereof:

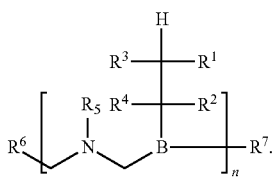

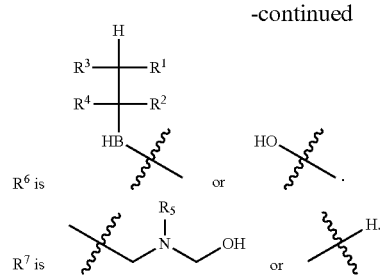

Each instance of $R^1$, $R^2$, $R^3$, and $R^4$ is independently —H or substituted or unsubstituted alkyl, cycloalkyl, alkenyl, alkoxyl, aryl, heterocyclyl or $R^3$ and $R^4$ combine to form a 5-membered cycloalkyl or heterocyclyl or 6-membered aryl, cycloalkyl or heterocyclyl. Each instance of $R^5$ is independently —H, halo, or alkyl. n is a positive integer and the number average molecular weight or weight average molecular weight of the compound of formula (I) is between about 2,000 to about 80,000.

In some embodiments, a material includes compounds such as polyboroaminals of formula (II) or a salt or an adduct thereof:

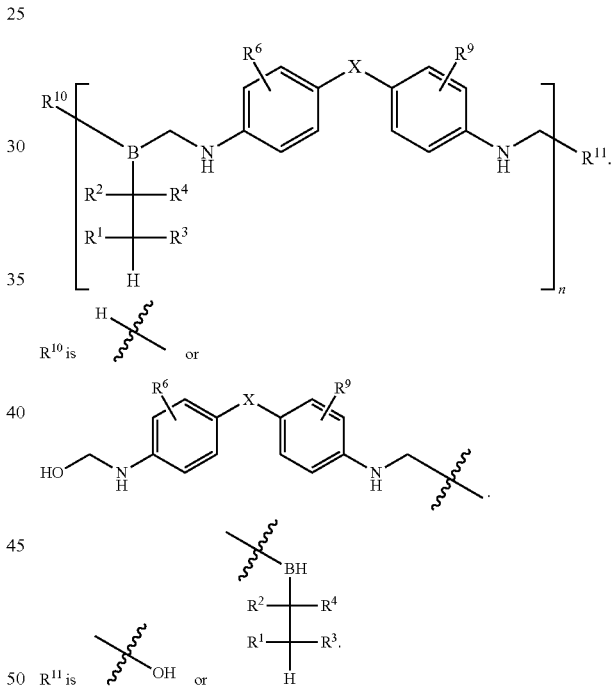

Each instance of $R^1$, $R^2$, $R^3$, and $R^4$ is independently —H or substituted or unsubstituted alkyl, cycloalkyl, alkenyl, alkoxyl, aryl, heterocyclyl or $R^3$ and $R^4$ combine to form a 5-membered cycloalkyl or heterocyclyl or 6-membered aryl, cycloalkyl or heterocyclyl. Each instance of $R^6$ and $R^9$ are independently —H, halo, nitro, or substituted or unsubstituted alkyl, cycloalkyl, alkenyl, alkoxyl, aryl, or heterocyclyl. Each instance of X is substituted or unsubstituted alkyl,

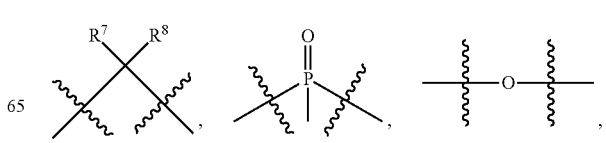

-continued

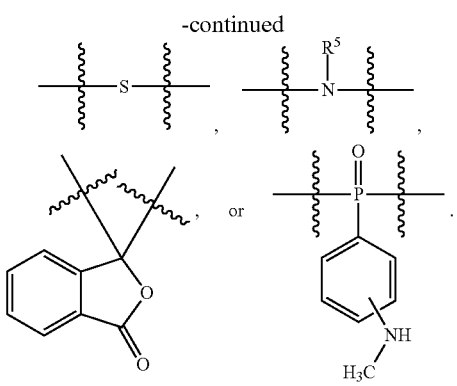

Each instance of $R^7$ and $R^8$ is independently —H, halo, nitro, or substituted or unsubstituted alkyl, cycloalkyl, alkenyl, alkoxyl, aryl, or heterocyclyl. Each instance of $R^5$ is independently selected from the group consisting of —H, halo, and alkyl. n is a positive integer and the number average molecular weight or weight average molecular weight of the compound of formula (II) is between about 2,000 to about 80,000.

DETAILED DESCRIPTION

Embodiments described herein generally relate to polythioaminals and synthesis of polythioaminals. Compounds, compositions, and methods described herein may take advantage of diol-containing monomers for achieving polythioaminals having improved and tailorable physical and mechanical properties.

As used herein, "alkyl" includes an acyclic alkyl moiety containing 1, 2, 3, 4, 5, 6, 7, 8, 9, 10, or more carbon atoms. In some embodiments, alkyl is a C1-C10 alkyl or a C1-C6 alkyl. Examples of alkyl groups include, but are not limited to, methylene, ethylene, propylene, isopropylene, butylene, isobutylene, t-butylene, pentylene, hexylene, heptylene, octylene, nonylene, and decylene.

As used herein, "aryl" includes any monocyclic, bicyclic, or tricyclic carbon ring of up to about 10 carbon atoms in each ring, such as 6 carbon atoms, wherein at least one ring is aromatic, or an aromatic ring system of 5 to 14 carbon atoms which includes a carbocyclic aromatic group fused with a 5- or 6-membered cycloalkyl group. Examples of aryl groups include, but are not limited to, phenyl, naphthyl, tetrahydronaphthyl and indanyl.

As used herein, "cycloalkyl" includes a hydrocarbyl group containing at least one saturated or partially unsaturated ring structure, which may be attached to another chemical structure via a carbon atom in the ring structure. In some embodiments, cycloalkyl includes a saturated or a partially unsaturated C3-C12 cyclic moiety. Examples of cycloalkyl groups include, but are not limited to, cyclopropyl, cyclobutyl, cyclopentyl, cyclopentenyl, cyclohexyl, cyclohexenyl, cycloheptyl, cycloheptenyl, cyclooctenyl, and cyclooctyl.

As used herein, "heterocyclyl" includes saturated, partially unsaturated, or fully unsaturated monocyclic, bicyclic or tricyclic group of 2 to 14 ring-carbon atoms and, in addition to ring-carbon atoms, 1 to 4 heteroatoms selected from P, N, O, and S. In some embodiments, the heterocyclic group is bonded to another moiety through carbon or through a heteroatom. Examples of heterocyclyl include, but are not limited to, pyrrolidinyl, imidazolidinyl, piperidinyl, piperazinyl, tetrahydrofuranyl, morpholinyl, thiazolidinyl, pyridinyl, thienyl, furanyl, pyrimidinyl, imidazolyl, pyrazolyl, thiazolyl, thiadiazolyl, isothiazolyl, oxazolyl, isoxazolyl, oxadiazolyl, pyrrolyl, pyridazinyl, pyrazinyl, quinolinyl, isoquinolinyl, benzofuranyl, benzothienyl, triazinyl, indolyl, benzothiazolyl, benzooxazolyl, benzimidazolyl, isoindolyl, and benzotriazolyl.

As used herein, "alkoxyl" includes RO— where R is alkyl. "Alkoxy" includes, but is not limited to, methoxy, ethoxy, propoxy, isopropoxy, butoxy and isobutoxy.

As used herein, "alkenyl" includes an alkyl moiety having at least one carbon-carbon double bound located along the alkyl moiety. Non-limiting examples of alkenyl include ethenyl, vinyl, allyl, propenyl, butenyl, pentenyl, hexenyl, heptenyl, octenyl, nonenyl, and decenyl.

Boron is a particularly attractive atom to introduce into the library of poly(aminal) chemistry because of its emergence as a particularly valuable moiety in biological and medical applications. For example, boron containing small molecules (such as carboaranes) have shown stealth-like properties when administered in-vivo, as the body does not recognize these small molecules, thereby having favorable pharmacokinetic properties. Furthermore, organoboron compounds have found applications such as neutron capture therapy for cancer treatment and tumor-targeting agents.

By providing a linear polymer containing a large percentage of boron atoms, one may anticipate these polymeric versions may also exhibit 'stealth-like' behavior for medical applications like their small molecule boron-containing counterparts. Access to linear polymers with a high density of boron provides access to many applications in the biomedical field.

Polyboroaminals of the present disclosure represent a new class of boron containing polymers. These polymers may be accessed through a step-growth polymerization of borane monomer and hexahydrotriazine monomer or in-situ generated imine. This polymerization therefore includes a boron containing monomer of the form R—$BH_2$ where R represents a spectrum of organic functional moieties (i.e. alkyl groups, alcohols, oligomers and polymeric forms). A diverse library of polymers with tailorable properties (such as thermal or mechanical properties) could be achieved by adjustments to the R-group as well as the substituents on the hexahydrotriazine monomer (or in-situ generated imine).

Bifunctional borane monomers ($BH_2$—R—$BH_2$) would be advantageous for synthesizing polyboroaminals. However, bifunctional borane monomers are not stable for prolonged periods of time and thus may not be commercially available and may require synthesis immediately before polymerization.

Although shown as neutral polyboroaminals in the structures and schemes, the structures and schemes of the present disclosure fully embrace polyboroaminals that are salts, such as pharmaceutically acceptable salts. Salts include polyboroaminals having one or more cations associated with each polyboroaminal. Salt forms of polyboroaminals may be formed by treating substantially neutral polyboroaminals with a salt such as metal hydroxides and/or metal halides. Upon treatment with a salt, a polyboroaminal salt may be formed with a hydroxide and/or halide coordinated to a boron atom of the polyboroaminal (forming a negatively charged polyboroaminal boronate) and a metal ion coordinated to the negatively charged boronate moiety. A counterion of a polyboroaminal that is a salt includes, but is not limited to, cations such as $Na^+$, $K^+$, $Li^+$, $Mg^{2+}$, $Ca^{2+}$ and mixtures thereof. The salt forms of polyboroaminals of the present disclosure find particular advantage for medical applications due to improved water solubility as compared to a substantially neutral polyboroaminal.

Applications of polyboroaminals of the present disclosure include, but are not limited to, tissue engineering applications and subcutaneous injection for sustained release of a medicine over a period of time. Polyboroaminals of the present disclosure provide polymers having controllable release of medicinal cargo and controllable polymer degradation (pharmacokinetics) of the polymers. For example, reactive oxygen species (ROS) are present in increased amounts in and around cancerous tumors. Polyboroaminals of the present disclosure may react with ROS which allows selective delivery of a medicinal cargo to a tumor and breakdown of the polyboroaminal at the tumor site (improved pharmacokinetics as compared to polythioaminals). Furthermore, polyboroaminals of the present disclosure have enhanced permeability and retention to tumor cells (as compared to polythioaminals) due in part of the presence of stealth-like boron.

Polyboroaminals of the present disclosure include polyboroaminals of the general formula (I):

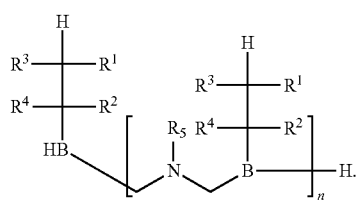

(I)

Each instance of $R^1$, $R^2$, $R^3$, and $R^4$ is independently —H or substituted or unsubstituted alkyl, cycloalkyl, alkenyl, alkoxyl, aryl, or heterocyclyl or $R^3$ and $R^4$ may combine to form a 5-membered cycloalkyl or heterocyclyl or 6-membered aryl, cycloalkyl or heterocyclyl. For substituted $R^1$, $R^2$, $R^3$, and $R^4$, substituents include alkyl, aryl, alkoxyl, halo, cycloalkyl, and heterocyclyl. Each instance of $R^5$ is independently —H, halo, or alkyl group such as methyl, ethyl, propyl, butyl, pentyl, hexyl, or cyclohexyl. As used herein, "halo" includes —F, —Cl, —Br, and —I. $R^5$ may be substituted or unsubstituted. For substituted $R^5$, substituents include alkyl, aryl, alkoxyl, halo, cycloalkyl, and heterocyclyl. $R^5$ may be substituted with one or more —$NH_2$ moieties. One or more of the —$NH_2$ moieties can form an imine upon treatment with paraformaldehyde. The imines may then form a hexahydrotriazine.

In some embodiments, 'n' of polythioaminals of the general formula (I) is a positive integer such that the number average molecular weight (Mn) or weight average molecular weight (Mw) of the polythioaminal is between about 2,000 to about 80,000, about 5,500 to about 40,000, such as between about 10,000 to about 25,000, between about 15,000 to about 20,000.

Polyboroaminals of the present disclosure include polyboroaminals of the general formula (II):

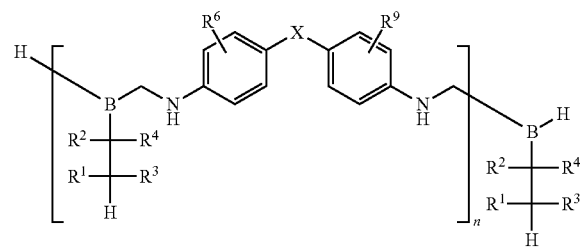

(II)

In general formula (II), $R^1$, $R^2$, $R^3$, and $R^4$ are as described above. $R^6$ and $R^9$ are independently —H, halo, nitro, or substituted or unsubstituted alkyl, cycloalkyl, alkenyl, alkoxyl, aryl, or heterocyclyl. For substituted $R^6$ and $R^9$, substituents include alkyl, aryl, alkoxyl, halo, cycloalkyl, and heterocyclyl. X is substituted or unsubstituted alkyl,

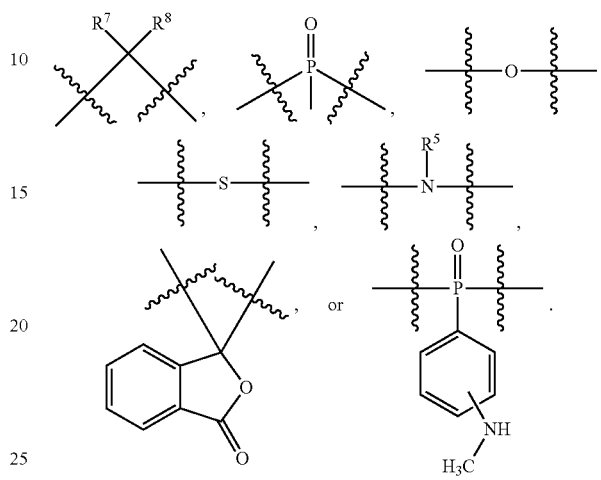

$R^7$ and $R^8$ are independently —H, halo, nitro, or substituted or unsubstituted alkyl, cycloalkyl, alkenyl, alkoxyl, aryl, or heterocyclyl. For substituted $R^7$ and $R^8$, substituents include alkyl, aryl, alkoxyl, halo, cycloalkyl, and heterocyclyl. $R^5$ is as described above. For substituted X groups, substituents include alkyl, aryl, alkoxyl, halo, cycloalkyl, and heterocyclyl.

In some embodiments, 'n' of polythioaminals of the general formula (II) is a positive integer such that the number average molecular weight (Mn) or weight average molecular weight (Mw) of the polythioaminal is between about 2,000 to about 80,000, about 5,500 to about 40,000, such as between about 10,000 to about 25,000, between about 15,000 to about 20,000.

Polyboroaminal formation of the present disclosure may proceed as a neat mixture of starting material or may be performed in a solvent or mixtures of solvents, to control viscosity. Polar aprotic solvents such as N-methyl-2-pyrrolidone (NMP), dimethylsulfoxide (DMSO), N,N-dimethylformamide (DMF), N,N-dimethylacetamide (DMA), propylene carbonate (PC), propylene glycol methyl ether acetate (PGMEA) or mixtures thereof, may be used. The aforementioned polar solvents may be used to dissolve paraformaldehyde.

In other embodiments, a low polarity or non-polar aprotic solvent may be used to produce a polyboroaminal, such as tetrahydrofuran, dimethyl ether, methylene chloride, toluene, benzene, and kerosene.

In some embodiments, a reaction mixture comprises a diamine that reacts to form a polyhexahydrotriazine (PHT) as shown in Scheme 1. In some embodiments, the α-terminus and/or ω-terminus of a diamine reacts with an aldehyde to form an imine intermediate, and the imine intermediate then forms a hexahydrotriazine linkage upon reaction of the imine intermediate with two other imine intermediates present in the reaction mixture.

$H_2N$—X—$NH_2$ 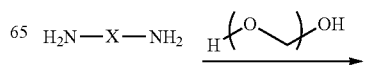

-continued

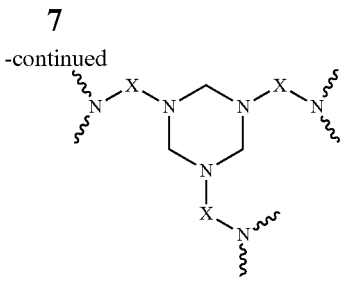

As described herein, an α-terminus and ω-terminus refer to opposing ends of a molecule or polymer. The reaction of Scheme 1 is typically performed at a temperature above 50° C., such as about 200° C., to form the PHT. As shown in Scheme 1, hexahydrotriazines may be formed by the reaction of primary diamines with paraformaldehyde to form diimines which then form hexahydrotriazines. Alternatively, hexahydrotriazines may be formed by the reaction of primary monoamines with paraformaldehyde to form imines which then form hexahydrotriazines. Monoamine and diamine monomers, and other reactive monomers described herein, may serve as reactive diluent(s) for polymerization reactions allowing for solution processing of oligomers and polymers described herein.

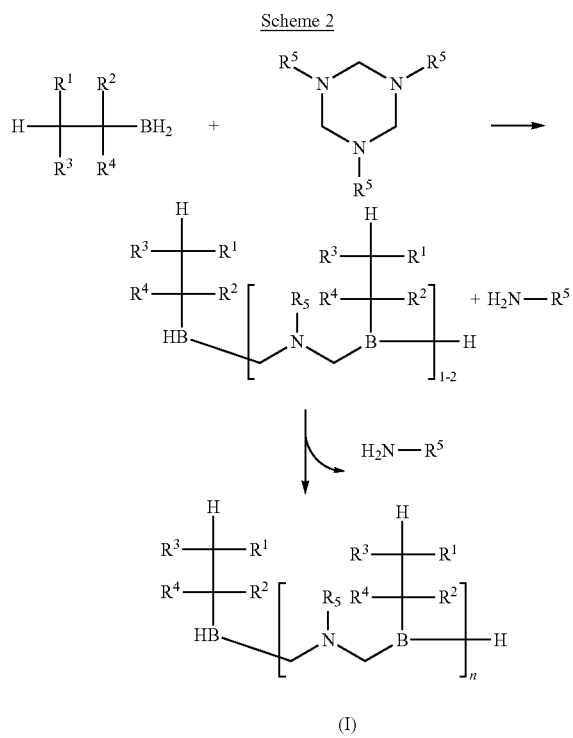

Scheme 2 illustrates polyboroaminal formation from a borane monomer and hexahydrotriazine. Polyboroaminal formation may be promoted with the application of heat to the reaction mixture. For Scheme 2, $R^1$, $R^2$, $R^3$, $R^4$, and $R^5$ are as described above. The hexahydrotriazines may be formed in situ. As shown in Scheme 2, reaction of the borane monomer with hexahydrotriazine yields a low molecular weight polyboroaminal and amine byproduct. The amine byproduct may be removed in vacuo and/or by the presence of any suitable amine scavenger, allowing higher molecular weight polyboroaminals (such as the formula of formula (I)) to be formed.

In some embodiments, polymerization to form polyboroaminals proceeds using hexahydrotriazine monomers by heating (to about 85° C.) in a sealed reaction vessel to begin the generation of oligomers over a period of time (for example, about 18 hrs). Then, a vacuum may be applied to remove the generated small molecule amine from the reaction and driving the polymerization to higher molecular weight (Scheme 2).

Scheme 3 illustrates, an example polyboroaminal synthesis using starting materials where each of $R^1$, $R^2$, $R^3$, $R^4$, and $R^5$ is methyl (—CH$_3$).

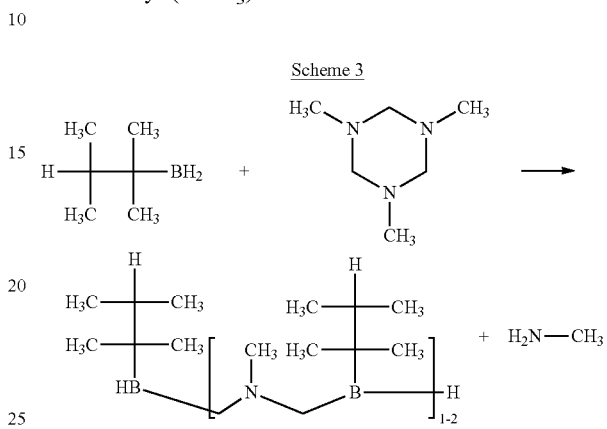

As shown in Scheme 3, reaction of the borane monomer with hexahydrotriazine yields a low molecular weight polyboroaminal and amine byproduct. The amine byproduct may be removed in vacuo and/or by the presence of an amine scavenger, allowing the higher molecular weight polyboroaminals shown in Scheme 3 to be formed. For Scheme 3, 'n' is as described above.

As noted above, an alternative synthetic route to access polyboroaminals is the utilization of diamine monomers to form stable imines when reacted with paraformaldehyde. For example, aromatic amines substituted with electron withdrawing groups, such as nitro groups or fluorinated substituents may be used. Aliphatic amines yield the formation of triazines when reacted with paraformaldehyde. As shown in Scheme 4, aromatic diamines may yield the formation of aromatic diimines. The diimine yields polyboroaminals of formula (II) upon treatment with a borane monomer.

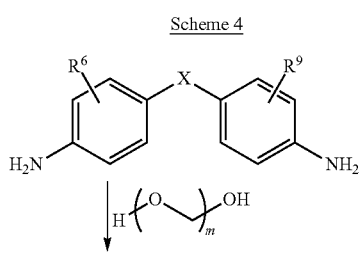

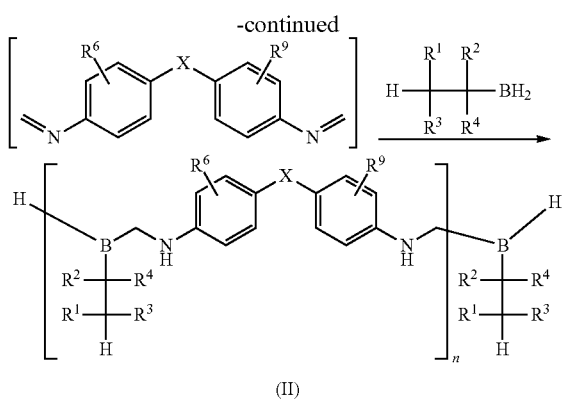

(II)

For Scheme 4, $R^1$, $R^2$, $R^3$, $R^4$, $R^6$, $R^9$, and X are as described above. In some embodiments, polymerization of imine monomers is accomplished with one of two different approaches: (i) a one pot approach in which the imine is generated in situ by reaction with paraformaldehyde followed by subsequent reaction by the borane monomer or (ii) the imine could first be generated by reaction with paraformaldehyde then isolated or purified then subsequently reacted with the borane monomer. Selection of either method may be starting material specific, and contingent on both the stability of the imine generated and the stability of the borane monomer. Either method has distinct advantages. The one pot method is elegant and simple but may require higher temperatures to crack the paraformaldehyde and react the resulting formaldehyde with diamine. The second method would be more work intensive but isolation of the imine monomer may allow running polymerizations at lower temperatures and provide access to a wider range of polymers made from more thermally sensitive monomers.

Borane monomers of the present disclosure may be synthesized by hydroboration of alkenes, as shown in Scheme 5.

Scheme 5

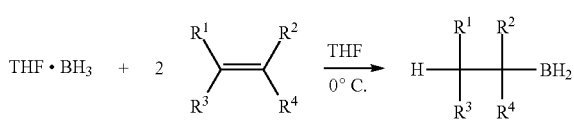

One method to synthesize these borane containing monomers can be accomplished by starting with a borane tetrahydrofuran complex, as shown in Scheme 5. At reduced temperature, such as 0° C., the addition of a selected functionality containing an alkene moiety generates the targeted borane monomer quantitatively. The borane monomer may be formed in situ followed by subsequent reaction of the borane monomer with a hexahydrotriazine and/or imine/diimine to yield polyboroaminals. Given the stability of the boron containing monomer, lower temperatures may be utilized to access polyboroaminals which would make reaction with imines an alternative/additional synthetic method.

For polyboroaminal formation, the order and rate of addition of the starting material may be adjusted, and the reaction mixture may be heated at a temperature from about 50° C. to about 150° C., for a time period from about 1 hour to about 24 hours, such as at a temperature of about 85° C. for about 18 hours. The temperature of the reaction may be adjusted depending on the boiling point of the solvent, and/or if reflux conditions are desired. Isolation and purification of the polyboroaminal may be achieved by cooling the reaction mixture, followed by precipitation and washing in any suitable suitable solvent and drying. The polyboroaminal product(s) may be redissolved in a suitable deuterated solvent for nuclear magnetic resonance experiments, such as DOSY-NMR and/or other 2D NMR techniques to analyze the polymer product and identify the peaks corresponding to the repeat unit moieties. Gel permeation chromatography (GPC) may also be used to determine the number average molecular weight of the substituted polymer. In some embodiments, polythioaminals of the present disclosure have a polydispersity index (PDI) of between about 1.00 to about 1.2, for example about 1.05.

As an exemplary process for polyboroaminal formation, in a stirred vessel, the borane monomer is added to 1.3 equivalents of the triazine precursor. The vessel is purged with nitrogen or other inert gas and sealed, and the reaction mixture is heated to about 85° C. The reaction mixture is maintained at about 85° C. for about 18 hours to form polyboroaminal(s). Vacuum is then applied to the vessel to remove volatile byproducts, driving growth in molecular weight of the resulting polymer molecules according to LeChatelier's Principle. The reaction is allowed to proceed for about 24 hours, during which stirring may cease due to viscosity of the mixture. The resulting polymer is typically optically transparent and may range from a solid to a viscous liquid.

Polyboroaminals of the present disclosure may be terminated at the boron α- and/or ω-termini with any suitable boron reactive species. In some embodiments, polyboroaminals of formulas (I) or (II) are hydroxyl terminated at the α- and/or ω-termini to form polyboroaminals of formulas (III) or (IV). In some embodiments, polyboroaminals of formulas (I) or (II) are bonded to a therapeutic agent, such as a medicine. Bonds include covalent bonds, ionic bonds, and/or hydrogen bonds. As a non-limiting example, polyboroaminals of formulas (I) or (II) are terminated at the α- and/or ω-termini with a therapeutic agent.

Scheme 6 illustrates end capping of a polyboroaminal. As shown in Scheme 6, a polyboroaminal of formula (I) is treated with a peroxide to yield α- and/or ω-hydroxyl-capped polyboroaminals of formulas (III) and (IV).

Scheme 6

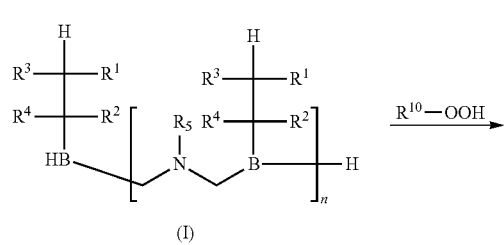

(I)

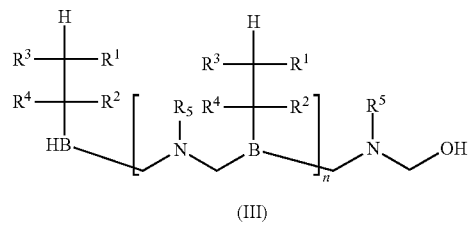

(III)

+

-continued

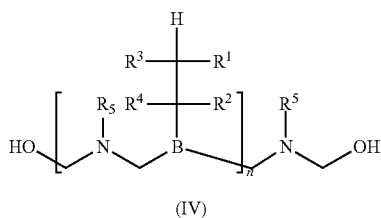

(IV)

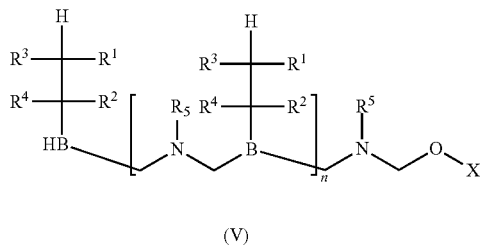

(V)

+

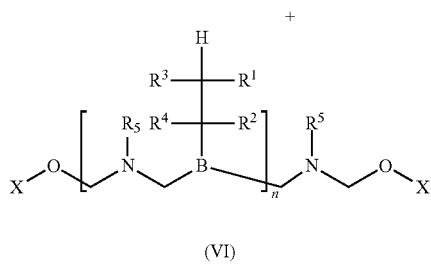

(VI)

$R^{10}$ includes substituted or unsubstituted —H, phenylcarbonyl, alkyl, and phenyl. For substituted $R^{10}$, substituents include alkyl, aryl, alkoxyl, halo, cycloalkyl, and heterocyclyl.

For example, $R^{10}$—OOH may be meta-chloroperoxybenzoic acid (MCPBA). For polyboroaminals of formulas (III), (IV), (V), and (VI), $R^1$, $R^2$, $R^3$, $R^4$, and $R^5$ are the same as described above. α- and/or ω-hydroxyl-capped polyboroaminals of formulas (III) and (IV) may then be capped with an X substituent to yield polyboroaminals of formulas (V) and (VI). X may be any suitable alcohol reactive species. Of particular use, X may be a therapeutic agent for treating a medical condition. X may be an alkane thiol, an aromatic thiol such as a thiophenol or a thioaniline, a peptide, a protein, a thio-acid, a nucleotide, or combinations thereof. X may be a reactive or non-reactive species, a cargo, a linking group, a medicine, a functional species for further modification after construction of the polymer of formula (V) or the polymer of formula (VI), a polymerization starter, a chemical species capable of initiating depolymerization, or a combination thereof. Any of the above species may act as a linking species or group that links one or more polyboroaminals to each other.

Scheme 7 illustrates end capping of a polyboroaminal. As shown in Scheme 7, a polyboroaminal of formula (II) is treated with a peroxide to yield α- and/or ω-hydroxyl-capped polyboroaminals of formulas (VII) and (VIII).

Scheme 7

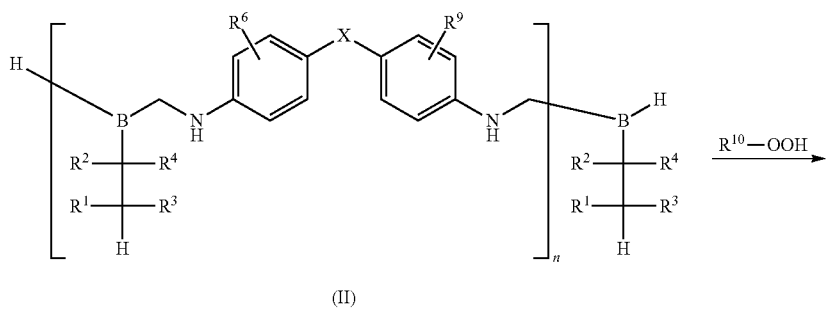

(II)

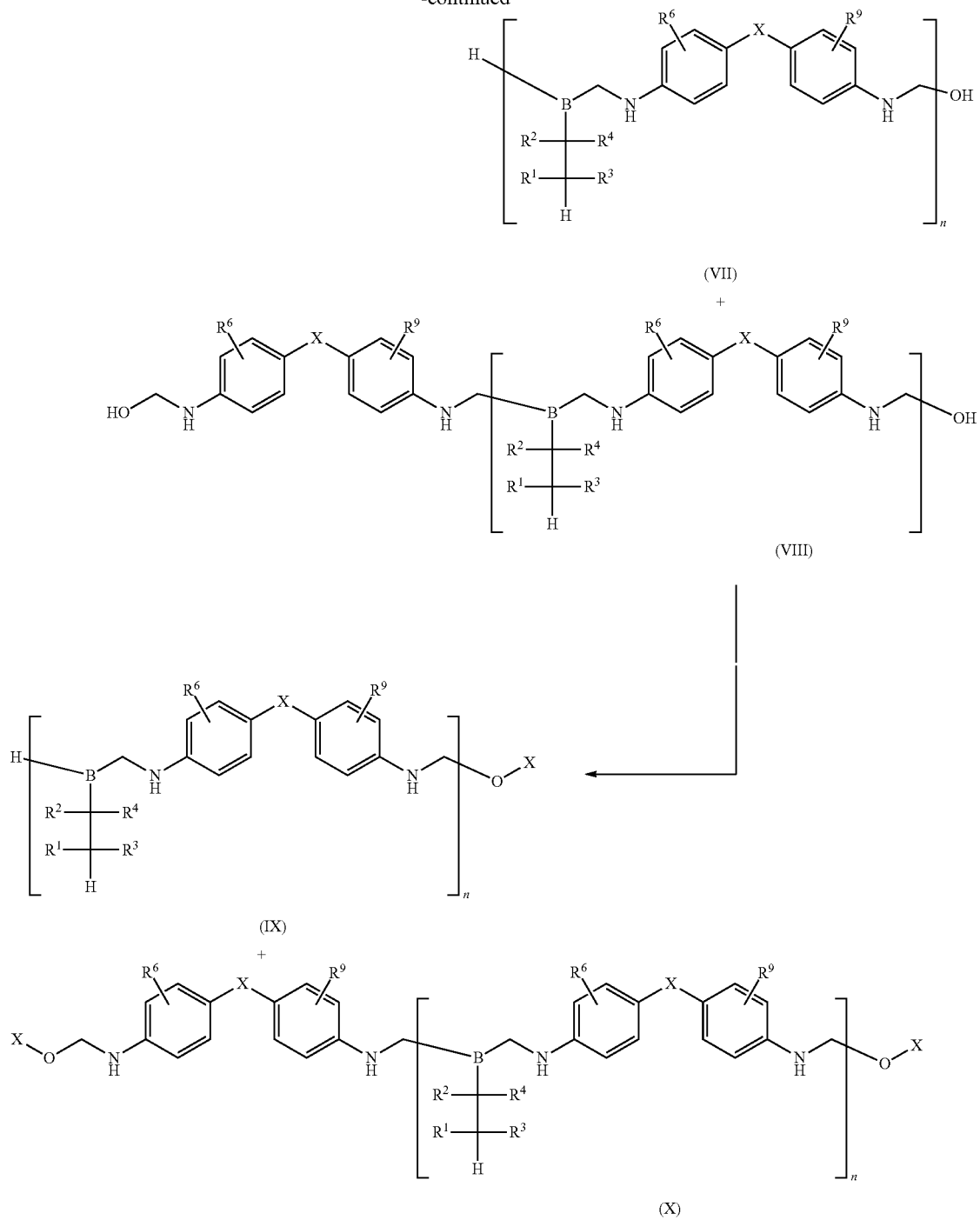

For Scheme 7, $R^{10}$ is the same as described above. For polyboroaminals of formulas (II), (VII), (VIII), (IX), and (X), $R^1$, $R^2$, $R^3$, $R^4$, and $R^5$ are the same as described above. α- and/or ω-hydroxyl-capped polyboroaminals of formulas (VII) and (VIII) may then be capped with an X substituent to yield polyboroaminal adducts of formulas (VIII) and (X). X may be any suitable alcohol reactive species. Of particular use, X of polyboroaminal adducts of formulas (VIII) and (X) may be a therapeutic agent for treating a medical condition. X may be an alkane thiol, an aromatic thiol such as a thiophenol or a thioaniline, a peptide, a protein, a thio-acid, a nucleotide, or combinations thereof. X may be a reactive or non-reactive species, a cargo, a linking group, a medicine, a functional species for further modification after construction of the polymer of formula (IX) or the polymer of formula (X), a polymerization starter, a chemical species capable of initiating depolymerization, or a combination thereof. Any of the above species may act as a linking species or group that links one or more polyboroaminals to each other.

Polyboroaminals of the present disclosure represent a new class of boron containing polymers. These linear polymers may be accessed through a step-growth polymerization of borane monomer and hexahydrotriazine monomer or in-situ generated imine. A diverse library of polymers with tailorable properties (such as thermal or mechanical properties) is achieved. Applications of polyboroaminals of the present disclosure include, but are not limited to, tissue engineering applications and subcutaneous injection for sustained release of a medicine over a period of time. Polyboroaminals of the present disclosure provide polymers having controllable release of medicinal cargo and controllable polymer degradation (pharmacokinetics) of the polymers. Polyboroaminals of the present disclosure may react with ROS which allows selective delivery of a medicinal cargo to a tumor and breakdown of the polyboroaminal at the tumor site (improved pharmacokinetics as compared to polythioaminals). Furthermore, polyboroaminals of the present disclosure have enhanced permeability and retention to tumor cells (as compared to polythioaminals) due in part of the presence of stealth-like boron.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present invention, other and further embodiments of the invention may be devised without departing from the basic scope thereof, and the scope thereof is determined by the claims that follow.

What is claimed is:

1. A material comprising a compound of the formula, or a salt or an adduct thereof:

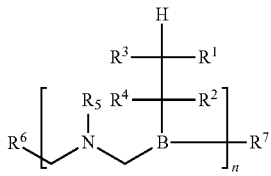

wherein:

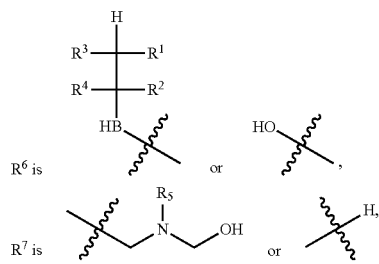

each instance of $R^1$, $R^2$, $R^3$, and $R^4$ is independently selected from the group consisting of —H or substituted or unsubstituted alkyl, cycloalkyl, alkenyl, alkoxyl, aryl, heterocyclyl or $R^3$ and $R^4$ combine to form a 5-membered cycloalkyl or heterocyclyl or 6-membered aryl, cycloalkyl or heterocyclyl, each instance of $R^5$ is independently selected from the group consisting of —H, halo, and substituted or unsubstituted alkyl, and n is a positive integer and the number average molecular weight or weight average molecular weight of the compound of the formula is between about 2,000 to about 80,000.

2. The material of claim 1, wherein at least one of $R^1$, $R^2$, $R^3$, or $R^4$ is substituted with a substituent selected from the group consisting of alkyl, aryl, alkoxyl, halo, cycloalkyl, heterocyclyl, and mixtures thereof.

3. The material of claim 1, wherein $R^5$ is alkyl, and is substituted with a substituent selected from the group consisting of alkyl, aryl, alkoxyl, halo, cycloalkyl, heterocyclyl, —NH$_2$ and mixtures thereof.

4. The material of claim 1, wherein n is a positive integer wherein the number average molecular weight or weight average molecular weight of the compound of the formula is between about 10,000 to about 25,000.

5. The material of claim 1, wherein the material is a salt of the compound.

6. The material of claim 5, wherein the salt comprises one or more cations selected from the group consisting of Na$^+$, K$^+$, Li$^+$, Mg$^{2+}$, Ca$^{2+}$ and mixtures thereof.

7. The material of claim 1, wherein the compound of the formula is bonded to a therapeutic agent.

8. A material comprising a compound of the formula, or a salt or an adduct thereof:

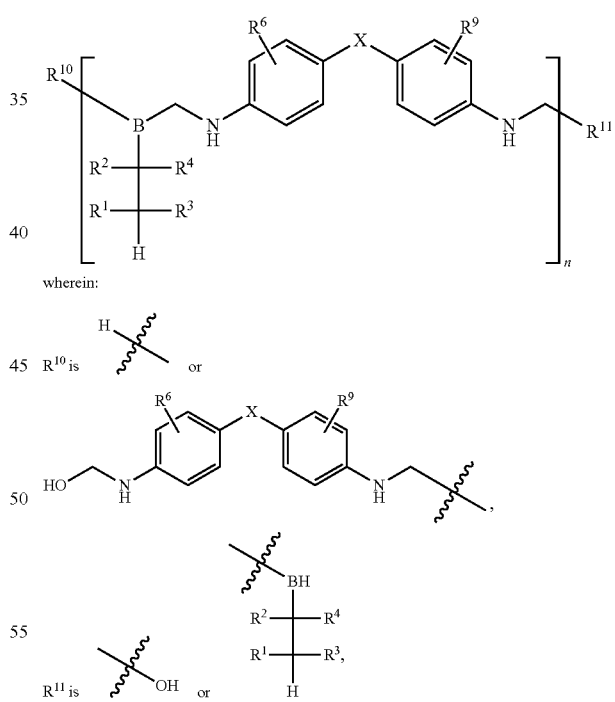

each instance of $R^1$, $R^2$, $R^3$, and $R^4$ is independently selected from the group consisting of —H or substituted or unsubstituted alkyl, cycloalkyl, alkenyl, alkoxyl, aryl, heterocyclyl or $R^3$ and $R^4$ combine to form a 5-membered cycloalkyl or heterocyclyl or 6-membered aryl, cycloalkyl or heterocyclyl, each instance of $R^6$ and $R^9$ are independently selected from the group consisting of —H, halo, nitro, or substituted or unsubstituted alkyl, cycloalkyl, alkenyl, alkoxyl, aryl, or heterocyclyl, each instance of X is independently selected from the group consisting of substituted or unsubstituted alkyl,

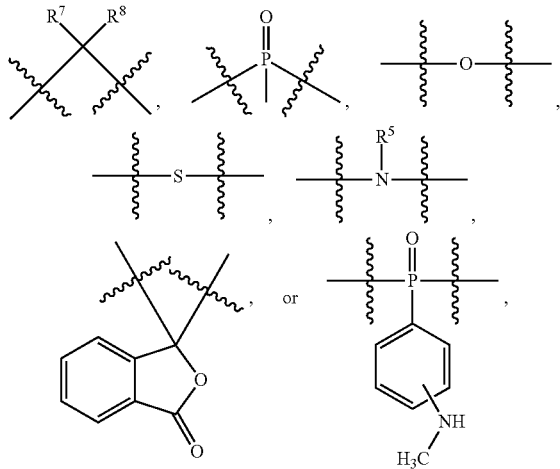

each instance of $R^7$ and $R^8$ is independently selected from the group consisting of —H, halo, nitro, or substituted or unsubstituted alkyl, cycloalkyl, alkenyl, alkoxyl, aryl, or heterocyclyl, each instance of $R^5$ is independently selected from the group consisting of —H, halo, and substituted or unsubstituted alkyl, and n is a positive integer and the number average molecular weight or weight average molecular weight of the compound of the formula is between about 2,000 to about 80,000.

9. The material of claim 8, wherein $R^6$ and $R^9$ is substituted with a substituent selected from the group consisting of alkyl, aryl, alkoxyl, halo, cycloalkyl, heterocyclyl, and mixtures thereof.

10. The material of claim 8, wherein $R^7$ and $R^8$ is substituted with a substituent selected from the group consisting of alkyl, aryl, alkoxyl, halo, cycloalkyl, heterocyclyl, and mixtures thereof.

11. The material of claim 8, wherein X is substituted with a substituent selected from the group consisting of alkyl, aryl, alkoxyl, halo, cycloalkyl, heterocyclyl, and mixtures thereof.

12. The material of claim 8, wherein at least one of $R^1$, $R^2$, $R^3$, or $R^4$ is substituted with a substituent selected from the group consisting of alkyl, aryl, alkoxyl, halo, cycloalkyl, heterocyclyl, and mixtures thereof.

13. The material of claim 8, wherein $R^5$ is alkyl and is substituted with a substituent selected from the group consisting of alkyl, aryl, alkoxyl, halo, cycloalkyl, heterocyclyl, —NH$_2$ and mixtures thereof.

14. The material of claim 8, wherein n is a positive integer wherein the number average molecular weight or weight average molecular weight of the compound of the formula is between about 10,000 to about 25,000.

15. The material of claim 8, wherein the material is a salt of the compound.

16. The material of claim 15, wherein the salt comprises one or more cations selected from the group consisting of Na$^+$, K$^+$, Li$^+$, Mg$^{2+}$, Ca$^{2+}$ and mixtures thereof.

17. The material of claim 8, wherein the compound of the formula is bonded to a therapeutic agent.

18. The material of claim 17, wherein $R^6$ and $R^9$ is substituted with a substituent selected from the group consisting of alkyl, aryl, alkoxyl, halo, cycloalkyl, heterocyclyl, and mixtures thereof.

19. The material of claim 17, wherein $R^7$ and $R^8$ is substituted with a substituent selected from the group consisting of alkyl, aryl, alkoxyl, halo, cycloalkyl, heterocyclyl, and mixtures thereof.

20. The material of claim 17, wherein X is substituted with a substituent selected from the group consisting of alkyl, aryl, alkoxyl, halo, cycloalkyl, heterocyclyl, and mixtures thereof.

21. The material of claim 17, wherein at least one of $R^1$, $R^2$, $R^3$, or $R^4$ is substituted with a substituent selected from the group consisting of alkyl, aryl, alkoxyl, halo, cycloalkyl, heterocyclyl, and mixtures thereof.

22. The material of claim 17, wherein $R^5$ is alkyl and is substituted with a substituent selected from the group consisting of alkyl, aryl, alkoxyl, halo, cycloalkyl, heterocyclyl, —NH$_2$ and mixtures thereof.

23. The material of claim 17, wherein the material is a salt of the compound.

24. The material of claim 23, wherein the salt comprises one or more cations selected from the group consisting of Na$^+$, K$^+$, Li$^+$, Mg$^{2+}$, Ca$^{2+}$ and mixtures thereof.

* * * * *